US00PP10866P

United States Patent [19]

Mendoza

[11] Patent Number: Plant 10,866

[45] Date of Patent: Apr. 27, 1999

[54] AGAPANTHUS PLANT NAMED 'HINAG'

[75] Inventor: Ramon Alaniz Mendoza, Santa Ana, Calif.

[73] Assignee: Hines Horticulture, Inc., Irvine, Calif.

[21] Appl. No.: 08/963,429

[22] Filed: Nov. 3, 1997

[51] Int. Cl.[6] ..... A01H 5/00

[52] U.S. Cl. ..... Plt./263

[58] Field of Search ..... Plt./68.1, 263

*Primary Examiner*—Howard J. Locker
*Assistant Examiner*—Melissa L. Kimball
*Attorney, Agent, or Firm*—C. A. Whealy

[57] ABSTRACT

A distinct cultivar of Agapanthus plant named 'Hinag', characterized by its low-growing, outwardly spreading, very dense and bushy growth habit; unique yellow and green variegated leaves; lavender blue flowers; numerous flowers and inflorescences per plant; and large, thick and fleshy roots.

2 Drawing Sheets

The present invention relates to a new and distinct cultivar of Agapanthus plant, botanically known as *Agapanthus africanus* and referred to by the cultivar name Hinag.

The new cultivar originated from a self-pollination made by the inventor of the *Agapanthus africanus* cultivar Peter Pan (not patented). The new Agapanthus was selected by the inventor from the progeny of this cross in a controlled environment in Santa Ana, Calif., in 1986. Plants of the new Agapanthus differ from plants of the parent cultivar in its variegated foliage as foliage of plants of the cultivar Peter Pan is solid green in color. In addition, plants of the new Agapanthus are more compact and have a slower growth rate than plants of the cultivar Peter Pan.

Asexual reproduction of the new cultivar by divisions taken at Santa Ana, Calif., has shown that the unique features of this new Agapanthus are stable and reproduced true to type in successive generations.

The following traits have been repeatedly observed and are determined to be the unique characteristics of 'Hinag'. These characteristics in combination distinguish 'Hinag' as a new and distinct cultivar:

1. Low-growing, outwardly spreading, very dense and bushy growth habit.
2. Unique yellow and green variegated leaves.
3. Lavender blue flowers; numerous flowers and inflorescences per plant.
4. Large, thick and fleshy roots.

Plants of the new Agapanthus can be compared to plants of the variegated Agapanthus cultivar Tinkerbell (not patented). However, in side-by-side comparisons conducted in Santa Ana, Calif., and Keller, Tex., plants of the new Agapanthus were lower growing and more floriferous than plants of the cultivar Tinkerbell. In addition, foliage of plants of the new Agapanthus is yellow and green in color whereas foliage of plants of the cultivar Tinkerbell is white and green in color.

The cultivar Hinag has not been observed under all possible environmental conditions. The phenotype may vary somewhat with variations in environment such as temperature and light intensity, without, however, any variance in genotype.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the first sheet comprises a side perspective view of a typical plant of 'Hinag'.

The photograph at the bottom of the first sheet is a side perspective view of typical inflorescences and leaves of 'Hinag'.

The photograph at the top of the second sheet comprises a close-up view of a typical inflorescence of 'Hinag'.

The photograph at the bottom of the second sheet comprises a comparison close-up view of a typical leaves of 'Hinag' (top) and 'Tinkerbell' (lower). Foliage and flower colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown outdoors in 3-gallon containers during the spring and summer in Santa Ana, Calif. and Keller, Tex. Measurements and numerical values represent averages for typical plants.

Botanical classification: *Agapanthus africanus* cultivar Hinag.

Parentage: Self-pollination of *Agapanthus africanus* cultivar Peter Pan (not patented).

Propagation:

*Type.*—Divisions.

*Time to initiate roots.*—About 20 days at 22° C.

*Time to develop roots.*—30 to 40 days at 22° C.

*Rooting habit.*—Large, thick and fleshy, about 1 cm in diameter.

Plant description:

*Appearance.*—Perennial herbaceous container and garden plant. Low-growing, but outwardly cascading. Dense and bushy growth habit. Leaves initially upright then outwardly arching. Flowers in umbels and held above the foliage on erect flower stems. Moderate growth rate.

*Plant height.*—About 25 cm.

*Plant spread.*—About 80 cm.

*Foliage description.*—Length, fully expanded leaves: About 42 cm. Width, fully expanded leaves: About 2 cm. Shape: Linear. Apex: Acute. Base: Sessile. Margin: Entire. Texture: Smooth. Color: Fully expanded leaves, upper surface: Margins: 11A/11B. Center and central stripes: 147A, overlaid with pale yellow. Fully expanded leaves, lower surface: Margins: 11B/

11C. Center and central stripes: 147A, overlaid with pale yellow.

Inflorescence description:

*Appearance.*—Umbel of lavender blue flowers. One inflorescence per flowering stem. Flowers held about 20 cm above the foliage on strong and thick scapes. Numerous flowers and numerous inflorescences per plant. Flowers not persistent. Flowers not fragrant.

*Flowering response.*—Under natural conditions, plants flower continuously from late spring through mid-summer.

*Flower longevity.*—Individual flowers typically last about one week.

*Quantity of flowers.*—Usually at least 50 flowers per inflorescence, numerous inflorescences per plant.

*Umbel size.*—About 10.5 cm.

*Flowers.*—Appearance: Tubular corolla of six fused tepals. Diameter: About 3.5 cm. Height: About 3 cm. Color: 92B with darker center stripes, 92A.

*Scapes.*—Aspect: Erect. Strength: Very strong. Length: About 45 cm. Diameter: About 1 cm. Color: 11B/147A overlaid with pale yellow.

*Pedicels.*—Length: About 2.5 cm. Diameter: About 1 mm. Color: 154C.

*Reproductive organs.*—Stamens: Quantity: Six. Length: About 2.3 cm. Color: White at base, bluish purple at apex. Pollen: Golden, moderate. Pistils: Style length: About 1.8 cm. Style color: White.

Disease resistance: Plants of the new Agapanthus have not been shown to be resistant to pathogens common to Agapanthus.

Seed production: Seed production has not been observed on plants of the new Agapanthus.

It is claimed:

1. A new and distinct cultivar of Agapanthus plant named 'Hinag', as illustrated and described.

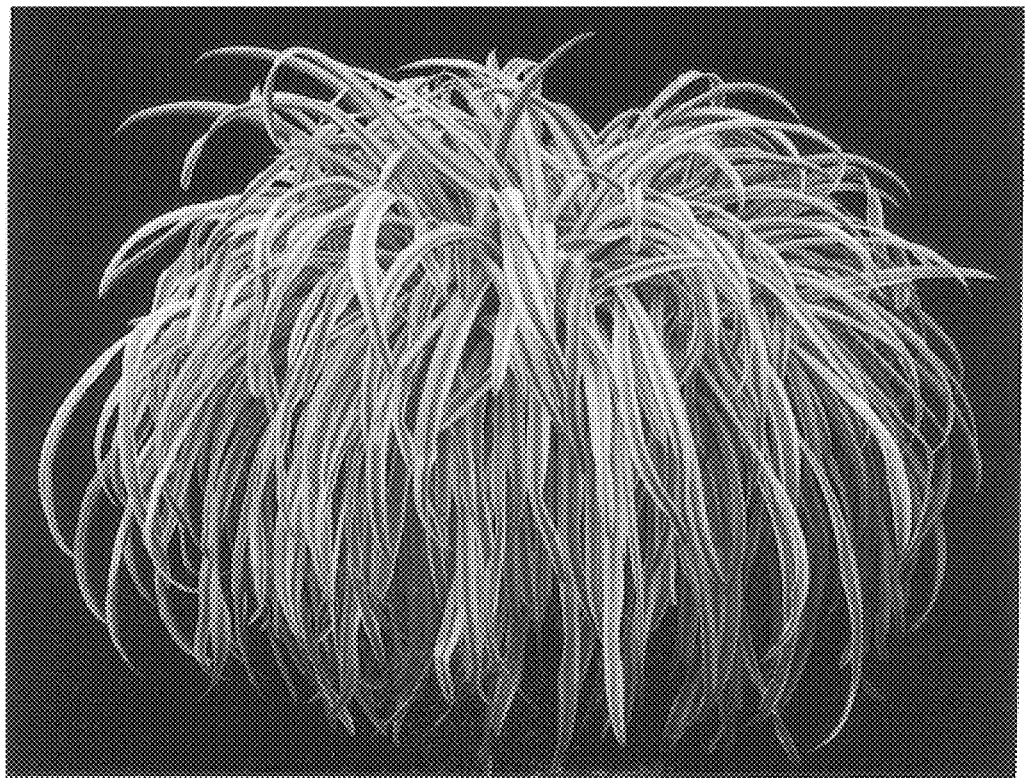
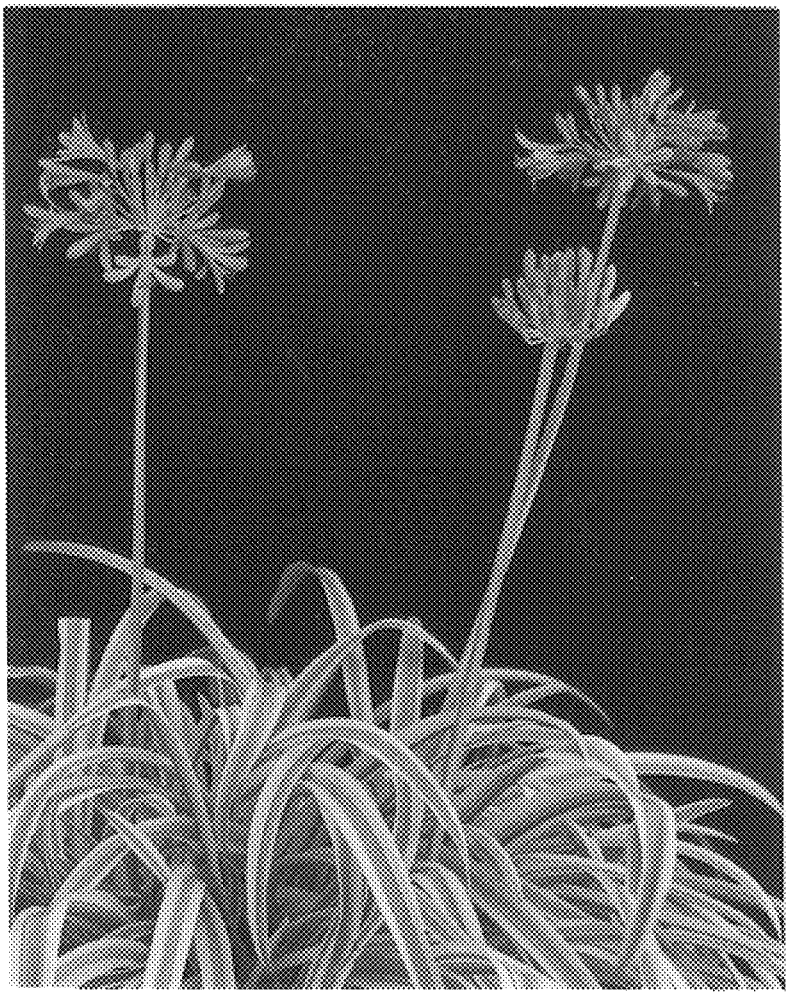

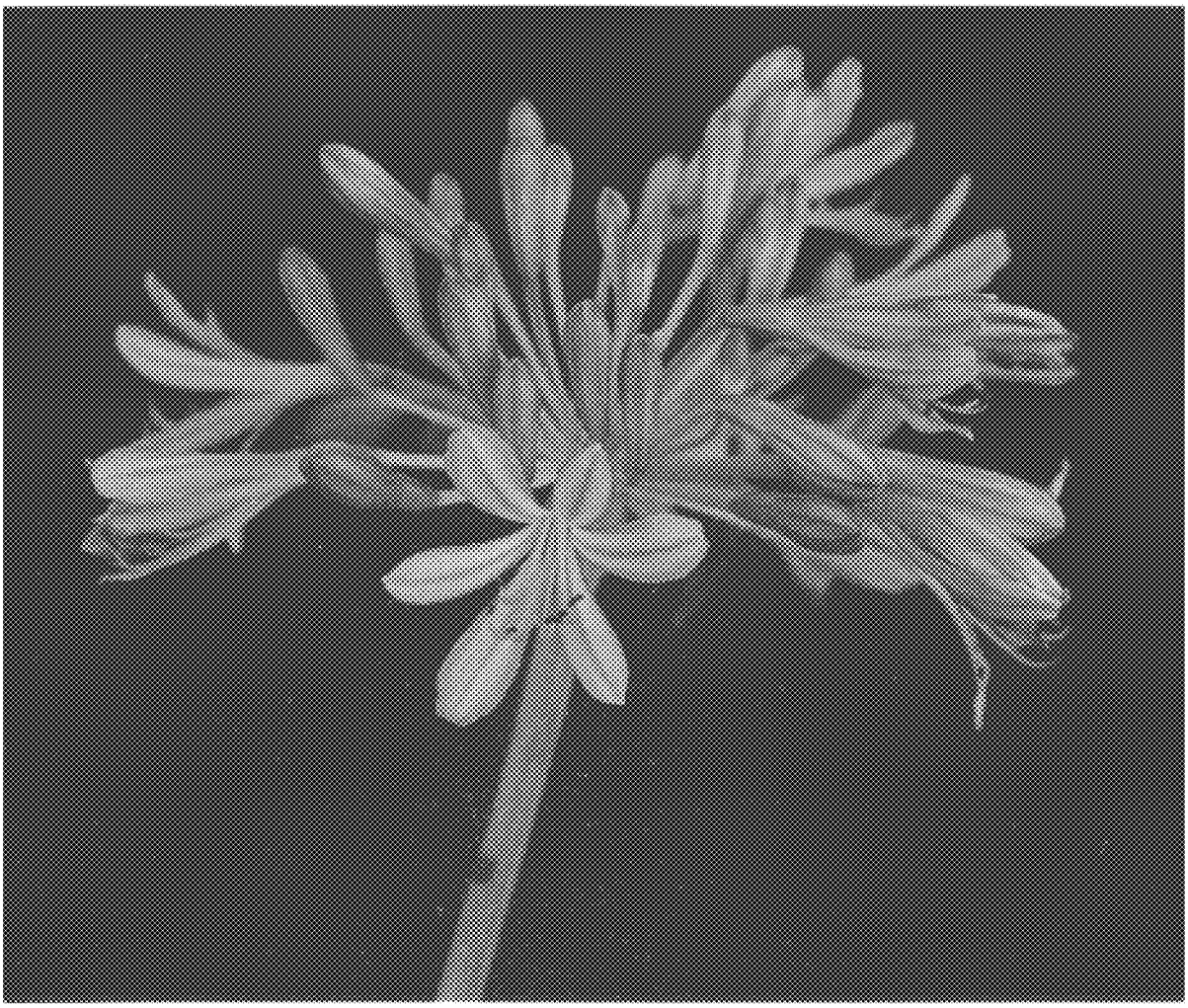
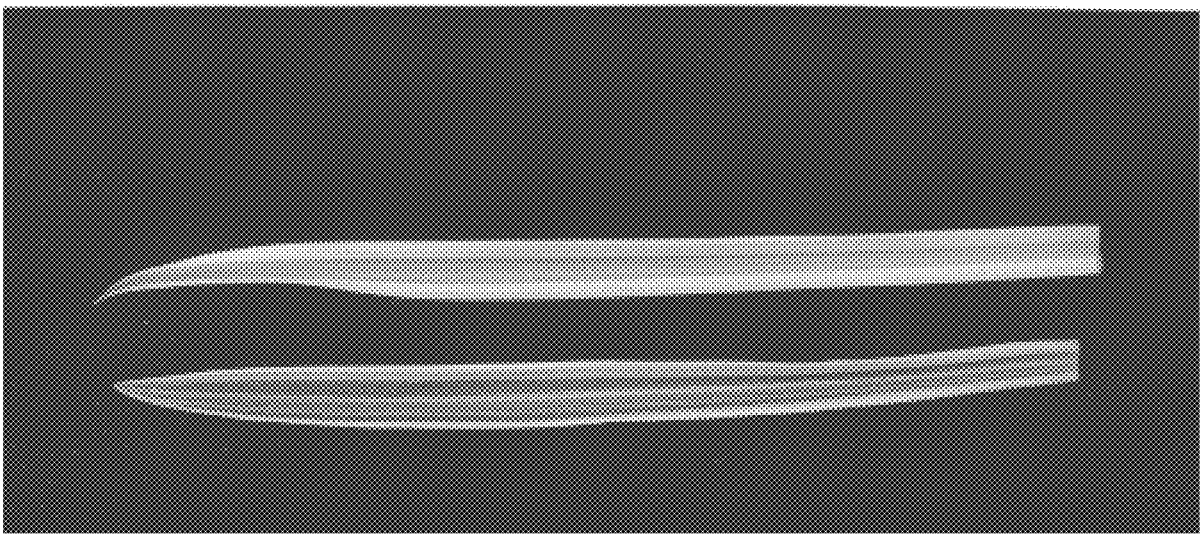

* * * * *